(12) United States Patent
Khan et al.

(10) Patent No.: US 7,595,167 B2
(45) Date of Patent: Sep. 29, 2009

(54) ALZHEIMER'S DISEASE-SPECIFIC ALTERATIONS OF THE ERK1/ERK2 PHOSPHORYLATION RATIO

(75) Inventors: Tapan Kumar Khan, Gaithersburg, MD (US); Daniel L. Alkon, Bethesda, MD (US)

(73) Assignee: Blanchette Rockefeller Neurosciences Institute, Morgantown, WV (US)

( * ) Notice: Subject to any disclaimer, the term of this patent is extended or adjusted under 35 U.S.C. 154(b) by 228 days.

(21) Appl. No.: 11/246,524

(22) Filed: Oct. 11, 2005

(65) Prior Publication Data

US 2007/0082366 A1  Apr. 12, 2007

(51) Int. Cl.
*G01N 33/567* (2006.01)
*G01N 33/561* (2006.01)
(52) U.S. Cl. .................................... 435/7.21
(58) Field of Classification Search ........................ None
See application file for complete search history.

(56) References Cited

U.S. PATENT DOCUMENTS

| 6,077,686 A * | 6/2000 | Der et al. ................... 435/69.1 |
| 6,107,050 A | 8/2000 | Alkon et al. |
| 2003/0153014 A1* | 8/2003 | Shen et al. .................. 435/7.9 |
| 2004/0014678 A1 | 1/2004 | Favit et al. |
| 2005/0059092 A1* | 3/2005 | Zhao et al. ................... 435/7.2 |

FOREIGN PATENT DOCUMENTS

| WO | WO 02/067764 A2 | 9/2002 |
| WO | WO 03/102016 A2 | 12/2003 |
| WO | 2007043998 | 4/2007 |
| WO | 2007044094 | 4/2007 |
| WO | 2007047029 | 4/2007 |

OTHER PUBLICATIONS

U.S. Appl. No. 12/083,056, filed Apr. 3, 2008.*
Partial International Search Report for PCT/US2006/037186 dated Feb. 5, 2007.
International Search Report and Written Opinion for PCT/US2006/022156 dated Feb. 8, 2007.
Frey, H.J. et al., "Problems Associated with Biological Markers of Alzheimer's Disease," Neurochemical Research, vol. 30, No. 12, Dec. 2005 (@ 2005), pp. 1501-1510.
Etcheberrigaray, R. et al., "Potassium channel dysfunction in fibroblasts identifies patients with Alzheimer disease," Proc. Natl. Acad. Sci. USA, vol. 90, pp. 8209-8213, Sep. 1993.
Neve, R. L. et al., Alzheimer's disease: dysfunction of a signalling pathway mediated by the amyloid precursor protein? Biochem. Soc. Symp. 67, 37-50, 2001.
McDonald, D.R. et al., "B-Amyloid Fibrils Activate Parallel Mitogen-Activated Protein Kinase Pathways in Microglia and THP1 Monocytes," The Journal of Neuroscience, Jun. 15, 1998, 18(12): 4451-4460.

Irizarry, M. C., "Biomarkers of Alzheimer Disease in Plasma," The Journal of the American Society for Experimental NeuroTherapeutics, vol. 1, 226-234, Apr. 2004.
Etcheberrigaray, R. et al., "Ionic and Signal Transduction Alterations in Alzheimer's Disease," Molecular Neurobiology, vol. 20, 1999.
Yang, C. et al., "Bradykinin-Induced p42/p44 MAPK Phosphorylation and Cell Proliferation via Src, EGF Receptors and P13-K/Akt in Vascular Smooth Muscle Cells," Journal of Cellular Physiology, 203:538-546 (2005).
Zhao, W. et al., "Impairment of phosphatase 2A contributes to the prolonged MAP kinase phosphorylation in Alzheimer's disease fibroblasts," Neurobiology of Disease, 14 (2003) 458-469.
de Leon, M. et al., "Biomarkers for the early diagnosis of Alzheimer's disease," Neurology, vol. 5, Mar. 2006.
Ito, E. et al., "Internal Ca2+ mobilization is altered in fibroblasts from patients with Alzheimer disease," Proc. Natl. Acad. Sci. USA, vol. 91, pp. 534-538, Jan. 1994.
Roux, P. P. et al., "ERK and p38 MAPK-Activated Protein Kinases: a Family of Protein Kinase with Diverse Biological Functions," Microbiology and Molecular Biology Reviews, Jun. 2004, p. 320-344, vol. 68, No. 2.
Etcheberrigaray, R. et al., "Therapeutic effects of PKC activators in Alzheimer's disease transgenic mice," PNAS, Jul. 27, 2004, vol. 101, No. 30, 11141-11146.
Thal, L. J. et al., "The Role of Biomarkers in Clinical Trials for Alzheimer Disease," Alzheimer Dis Assoc Disord, vol. 20, No. 1, Jan.-Mar. 2006.
Zhao, W. et al., "MAP Kinase Signaling Cascade Dysfunction Specific to Alzheimer's Disease in Fibroblasts," Neurobiology of Disease 11, 166-183 (2002).
Hetman M. et al., "Role of extracellular signal regulated kinases 1 and 2 in neuronal survival," Eur. J. Biochem, 271, 2050-2055 (2004) @ FBS 2004.
Hogervorst, E. et al., "The Validity and Reliability of 6 Sets of Clinical Criteria to Classify Alzheimer's Disease and Vascular Dementia in Cases Confirmed Post-Mortem: Added Value of a Decision Tree Approach," Dement Geriatr Cogn Disord 2003:16:170-180.
Chapman, P.F. et al., "Genes, models and Alzheimer's disease," Trends in Genetics, vol. 17, No. 5, May 2001.
Favit, A. et al., "Alzheimer's-specific effects of soluble B-amyloid on protein kinase C-a and -y degradation in human fibroblasts," Proc. Natl. Acad. Sci. USA, vol. 95, pp. 5562-5567, May 1998.

(Continued)

*Primary Examiner*—Daniel E. Kolker
(74) *Attorney, Agent, or Firm*—Milbank, Tweed, Haldey & McCloy LLP (57) ABSTRACT

The present invention is directed to a method of diagnosing Alzheimer's disease in a subject by detecting alterations in the ratio of specific phosphorylated MAP kinase proteins in cells after stimulation with a protein kinase C activator. The Alzheimer's disease-specific molecular biomarkers disclosed herein are useful for the diagnosis of Alzheimer's disease, monitoring the progression of Alzheimer's disease in a subject and in screening methods for the identification of compounds for treating or preventing Alzheimer's disease. The invention is also directed to kits containing reagents for the detection and diagnosis of Alzheimer's disease using the Alzheimer's disease-specific molecular biomarkers disclosed herein.

41 Claims, 2 Drawing Sheets

OTHER PUBLICATIONS

Oddo, S. et al., "Temporal Profile of Amyloid-B (AB) Oligomerization in an in Vivo Model of Alzheimer Disease—A Link Between AB and TAU Pathology," Journal of Biological Chemistry, vol. 281, No. 3, pp. 1599-1604, Jan. 20, 2006.

Pascale, A. et al., "Enhanced BK-induced calcium responsiveness in PC12 cells expressing the C100 fragment of the amyloid precursor protein," Molecular Brain Research 72 (1999) 205-213.

Etcheberrigaray, R. et al., "Calcium Responses in Fibroblasts from Asymptomatic Members of Alzheimer's Disease Families," Neurobiology of Disease 5, 37-45 (1998), Article No. NB980176.

Hirashima, N. et al., "Calcium Response in Human Fibroblasts: A Diagnostic Molecular Profile for Alzheimer's Disease," Neurobiology of Aging, vol. 17, No. 4, pp. 549-555, 1996.

Gibson, G. E. et al., Calcium stores in cultured fibroblasts and their changes with Alzheimer's disease, Biochimica et Biophysica Acta 1316 (1996) 71-77.

Berridge, M.J., "Inositol trisphosphate and diacylglycerol as second messengers," Biochem. J. (1984) 220, 345-360.

Bassa, B.V. et al., "Lysophosphatidylcholine activates mesangial cell PKC and MAP kinase by PLCy-1 and tyrosine kinase-Ras pathways," Am J Physiol 277, F328-338, 1999.

Lu, Q. et al., p44mpk MAP Kinase Induces Alzheimer Type Alterations in Tau Function and in Primary Hippocampal Neurons, Journal of Neuroscience Research 35:439-444 (1993).

Ekinci, F. et al., "Hyperactivation of Mitogen-Activated Protein Kinase Increases Phospho-Tau Immunoreactivity Within Human Neuroblastoma: Additive and Synergistic Influence of Alteration of Additional Kinase Activities," Cellular and Molecular Neurobiology, vol. 19, No. 2, 1999.

Grant, S. M. et al., "Phosphorylation of mitogen-activated protein kinase is altered in neuroectodermal cells overexpressing the human amyloid precursor protein 751 isoform," Molecular Brain Research 72 (1999) 115-120.

Barrow, P.A. et al., "Function Phenotype in Transgenic Mice Expressing Mutant Human Presenilin-1," Neurogiology of Disease 7, 119-126 (2000).

Biernat, J. et al., "Phosphorylation of Ser 262 Strongly Reduces Binding of Tau to Microtubules: Distinction between PHF-like Immunoreactivity and Microtubule Binding," Neuron, vol. 11, 153-163, Jul. 1993.

Cruzblanca, H. et al., "Bradykinin inhibits M current via phospholipase C and Ca2+ release from IP3-sensitive Ca1+ stores in rat sympathetic neurons," Proc. Natl. Acad. Sci. USA vol. 95, pp. 7151-7156, Jun. 1998.

Etcheberrigary, R. et al., "Molecular Mechanisms of Memory and the Pathophysiology of Alzheimer's Disease," Ann NY Acad Sci. 747:245-55, 1994.

Leissring, M. et al., "Capacitative Calcium Entry Deficits and Elevated Luminal Calcium Content in Mutant Presenilin-1 Knockin Mice," The Journal of Cell Biology, vol. 149, 2000.

Leissring, M. et al., "Presenilin-2 Mutations Modulate Amplitude and Kinetics of Inositol 1,4,5-Trisphosphate-mediated Calcium Signals," The Journal of Biological Chemistry, vol. 274, Nos. 46, Issue of Nov. 12, pp. 32535-32538, 1999.

Mattson, M.P. et al., Presenilin-1 Mutation Increases Neuronal Vulnerability to Focal Ischemia In Vivo and to Hypoxia and Glucose Deprivation in Cell Cuture: Involvement of Perturbed Calcium Homeostatis, The Journal of Neuroscience, Feb. 15, 2000, 20(4):1358-1364.

Putney, J.W. Jr., "Presenilins, Alzheimer's Disease, and Capacitative Calcium Entry," Neuron 27, 411-412, 2000.

Reynolds, C. H. et al., "Phosphorylation Sites on Tau Identified by Nanoelectrospray Mass Spectrometry: Differences In Vitro Between the Mitogen-Activated Protein Kinase ERK2, c-Jun N-Terminal Kinase and P38, and Glycogen Synthase Kinase-3B," J. Neurochem. 74, 1587-1595 (2000).

Sheehan, J.P. et al., "Calcium Homeostasis and Reactive Oxygen Species Production in Cells Transformed by Mitochondria from Individuals with Sporadic Alzheimer's Disease," The Journal of Neuroscience, Jun. 15, 1997 17(12):4612-4622.

Yoo, A.S. et al., "Presenilin-Mediated Modulation of Capacitative Calcium Entry," Neuron, vol. 27, 561-572, Sep. 2000.

Luigi, A. de et al., "Inflammatory markers in Alzheimer's disease and multi-infarct dementia," Mechanisms of Ageing and Development, 122 (2001) 1985-1995.

Anderson, I. et al., "Oxidative signalling and inflammatory pathways in Alzheimer's disease," Biochem. Soc. Symp. 67, 141-149, 2001.

Remarque, E.J. et al., "Patients with Alzheimer's disease display a pro-inflammatory phenotype," Experimental Gerontology 36 (2001) 171-176.

Bockman, S. et al., "Kinins and kinin receptors: importance for the activation of leukocytes," Journal of Leukocyte Biology, vol. 68, Nov. 2000.

Gasparini, L. et al., "Stimulation of B-Amyloid Precursor Trafficking by Insulin Reduces Intraneuronal B-Amyloid and Requires Mitogen-Activated Protein Kinase Signaling," The Journal of Neuroscience, Apr. 15, 2001, 21(8):2561-2570.

PCT International Search Report on PCT/US2005/036014, Oct. 19, 2006.

International Preliminary Report and Written Opinion for PCT/2005/036014 dated Apr. 24, 2008.

International Preliminary Report and Written Opinion for PCT/2006/022156 dated Apr. 24, 2008.

International Preliminary Report on Patentability and Written Opinion for PCT/US2006/037186 dated Apr. 16, 2008.

* cited by examiner

ALZHEIMER'S DISEASE-SPECIFIC ALTERATIONS OF THE ERK1/ERK2 PHOSPHORYLATION RATIO

FIELD OF THE INVENTION

The present invention relates to methods of diagnosing Alzheimer's disease in a subject by detecting alterations in the ratio of specific phosphorylated MAP kinase proteins in cells after stimulation with a protein kinase C activator. The Alzheimer's disease-specific molecular biomarkers disclosed herein are useful for the diagnosis of Alzheimer's disease, for monitoring disease progression and in screening methods for the identification of compounds for treating or preventing Alzheimer's disease.

BACKGROUND OF THE INVENTION

Perturbation of intracellular calcium homeostasis, increased levels of oxidative stress, and inflammatory mechanisms resulting in excitatory toxicity and neuronal death have been suggested to contribute to the pathogenesis of Alzheimer's disease (AD) (Ito et al. 1994, Putney, 2000; Yoo et al., 2000; Sheehan et al., 1997; De Luigi et al., 2001; Anderson et al., 2001; Remarque et al., 2001). A number of AD-associated abnormalities in intracellular $Ca^{2+}$ levels and other cellular processes have derived from studies using bradykinin as a stimulus. As a potent inflammation mediator, bradykinin (BK) is produced by brain and peripheral cells under pathophysiological conditions such as trauma, stroke, pain ischemia, and asthma (Regoli et al., 1993; Bockmann & Paegelow, 2000; Ellis et al., 1989; Kamiya et al., 1993). By acting on the B2 bradykinin receptor (BK2bR), a G-protein-coupled receptor, BK triggers phosphatidylinositol (PI) turnover through activity of phospholipase C (PLC), which in turn produces inositol 1, 4, 5-trisphospate (IP3) that increases intracellular $Ca^{2+}$ release from the IP3-sensitive stores (Noda et al., 1996; Venema et al., 1998; Wassdal et al., 1999; Cruzblanca et al., 1998; Ricupero et al., 1997; Pascale et al., 1999). Through the same pathway, BK also triggers production of other proinflammatory cytokines through activation of mitogen-activated protein (MAP) kinases (Hayashi et al., 2000; Schwaninger et al., 1999; Phagoo et al., 2001). Enhanced elevation of intracellular $Ca^{2+}$ levels has been found in AD brains as well as in AD peripheral cells in response to stimulation of bradykinin and inactivation of $K^+$ channels (Etcheberrigaray et al., 1993, 1998; Hirashima et al., 1996; Gibson et al., 1996(a)).

Stimulation of PLC subsequent to BK2bR activation also leads to production of diacylglycerol which, along with increased intracellular $Ca^{2+}$, activates protein kinase C (PKC) isoforms. The BK-activated PLC/phospholipids-$Ca^{2+}$/PKC cascade interacts with the Ras/Raf signaling pathway, which activates extracellular signal-regulated kinases 1/2 (Erk 1 and Erk2, which are referred to together as "Erk1/2"), a subtype of the MAP kinase family (Berridge, 1984; BAssa et al., 1999; Hayashi et al., 2000; Blaukat et al., 2000, Zhao et al. Neurobiology of Disease 11, 166-183, 2002). Erk1/2 receives signals from multiple signal transduction pathways and leads to cellular proliferation and differentiation by regulation of gene expression through a number of transcriptional factors, including AP-1, NF-κB, and cyclic AMP-responsive element binding protein (CREB). By acting as one of the major kinases, Erk2 phosphorylates tau at multiple serine/threonine sites including Ser-262 and Ser-356 (Reynolds et al., 1993; Lu et al., 1993). In addition, PKC-activated MAP kinase and BK receptor-associated pathways have been shown to regulate formation and secretion of the soluble form of amyloid precursor protein (sAPP) by different laboratories (Desdouits-Magnen et al., 1998; Gasparini et al., 2001; Nitsch et al., 1994, 1995, 1996, 1998). These findings have suggested the possibility that BK-associated sAPP processing may be linked to the PKC-MAP kinase pathway. On the other hand, pathological conditions such as viral infections, increased oxidative stress, aberrant expression of APP, and exposure to APβ cause activation of MAP kinase (Rodems & Spector, 1998; McDonald et al., 1998; Ekinci et al., 1999; Grant et al., 1999) and enhanced tau phosphorylation (Greenberg et al., 1994; Ekinci & Shea, 1999; Knowles et al., 1999). These effects implicate derangement of a MAP kinase signaling pathway(s) in the pathogenesis of AD.

Mitogen-activated protein kinases (such as Erk1 and Erk2) regulate phosphorylation of the microtubule associated protein tau and processing of the amyloid protein β, both events critical to the pathophysiology of Azheimer's disease. Enhanced and prolonged Erk1/2 phosphorylation in response to bradykinin has been detected in fibroblasts of both familial and sporadic Alzheimer's disease, but not age-matched controls (Zhao et al. Neurobiology of Disease 11, 166-183, 2002). Sustained Erk1/2 phosphorylation induced by bradykinin has previously been found in Alzheimer's disease fibroblasts and is the subject of WO 02/067764, which is herein incorporated by reference in its entirety.

There exists a need for highly sensitive and highly specific tests to diagnose Alzheimer's disease and to screen for compounds useful in the treatment and prevention of Alzheimer's disease. The present inventors have identified, for the first time, unique Alzheimer's disease-specific molecular biomarkers useful for the diagnosis of Alzheimer's disease in a highly sensitive and highly specific manner compared to previously known diagnostic tests. Thus, the unique Alzheimer's disease-specific molecular biomarkers disclosed herein serve as the basis for diagnostic methods having a high degree of sensitivity and specificity for the detection and diagnosis of Alzheimer's disease. The unique Alzheimer's disease-specific molecular biomarkers of the present invention are also useful in screening methods to identify compounds which may be used as therapeutic agents in the treatment and prevention of Alzheimer's disease.

SUMMARY OF THE INVENTION

The present invention is directed, in certain embodiments, to methods of diagnosing Alzheimer's disease in a subject comprising the steps of contacting cells obtained from a subject with an agent that is a protein kinase C activator and measuring the ratio of specific phosphorylated MAP kinase proteins in the cells to diagnose Alzheimer's disease in the subject. In a preferred embodiment, the ratio of specific phosphorylted MAP kinase proteins is a ratio between two phosphorylated MAP kinase proteins. In preferred embodiments, the diagnostic methods of the invention comprise an in vitro assay. In still further preferred embodiments of the diagnostic methods, the specific phosphorylated MAP kinase proteins are sequence variants of each other and belong to the same family of proteins.

In certain embodiments of the invention, the ratio of specific phosphorylated MAP kinase proteins is the ratio of phosphorylated Erk1 to phosphorylated Erk2 and is calculated by dividing the normalized amount of phosphorylated Erk1 by the normalized amount of phosphorylated Erk2. In preferred embodiments of the invention, the protein kinase C activator is selected from the group consisting of bradykinin, bryostatin, bombesin, cholecystokinin, thrombin, prostaglandin F2α and vasopressin.

In certain embodiments of the invention, the cells that are used in the diagnostic assays are peripheral cells. In preferred embodiments, the cells may be skin cells, skin fibroblast cells, blood cells or buccal mucosa cells. In certain embodiments, the cells are not isolated from cerebral spinal fluid. In other preferred embodiments, the cells do not comprise cerebral spinal fluid. In still other preferred embodiments, the cells are not obtained by a spinal tap or lumbar puncture.

In certain embodiments of the diagnostic methods, a protein kinase C activator is contacted with cells in media comprising serum. In other preferred embodiments of the invention, a protein kinase C activator is contacted with said cells in serum-free media.

In certain embodiments of the diagnostic methods of the invention, phosphorylated MAP kinase proteins are detected by immunoassay. In preferred embodiments of the invention, the immunoassay may be a radioimmunoassay, a Western blot assay, an immunofluoresence assay, an enzyme immunoassay, an immunoprecipitation assay, a chemiluminescence assay, an immunohistochemical assay, an immunoelectrophoresis assay, a dot blot assay, or a slot blot assay. In further preferred embodiments of the diagnostic methods of the invention, protein arrays or peptide arrays or protein micro arrays may be employed in the diagnostic methods.

In certain embodiments of the diagnostic methods of the invention, Alzheimer's disease may be diagnosed in a subject by contacting cells from the subject with an agent that is a protein kinase C activator and then measuring the ratio of a phosphorylated first MAP kinase protein to a phosphorylated second MAP kinase protein, wherein the phosphorylated first and phosphorylated second MAP kinase proteins are obtained from the cells after they have been contacted with the protein kinase C activator. In further embodiments of the diagnostic methods of the invention, the ratio of phosphorylated first MAP kinase protein to phosphorylated second MAP kinase protein in cells from the subject that have not been contacted with the protein kinase C activator is determined and this ratio is subtracted from the ratio of phosphorylated first and second MAP kinase proteins obtained from cells after they have been contacted with the protein kinase C activator to diagnose the presence of Alzheimer's disease in the subject based on the difference in the ratios. In preferred embodiments of the diagnostic methods of the invention, the difference in the ratios is diagnostic of Alzheimer's disease in the subject if the difference is a positive value.

In other preferred embodiments of the diagnostic methods of the invention, the difference is diagnostic of the absence of Alzheimer's disease in the subject if the difference is a negative value or zero.

Certain embodiments of the invention are directed to kits for diagnosing Alzheimer's disease in a subject. In certain embodiments of the invention, the kit may contain an agent that is a protein kinase C activator; in further embodiments of the invention, the kits may contain an antibody specific for a phosphorylated first MAP kinase protein. In still further embodiments of the invention, the kits may contain an antibody specific for a phosphorylated second MAP kinase protein. In preferred embodiments, the kits may contain any combination of the foregoing.

In certain embodiments of the invention, the kits for diagnosing Alzheimer's disease in a subject may contain one or more protein kinase C activators selected from the group consisting of bradykinin, bryostatin, bombesin, cholecystokinin, thrombin, prostaglandin F2α and vasopressin.

In certain embodiments of the invention, the kits for diagnosing Alzheimer's disease in a subject may contain antibodies specific for phosphorylated Erk1 or phosphorylated Erk2 or both. In preferred embodiments of the invention, the kit may contain anti-phospho-Erk1 antibody. In further preferred embodiments of the invention, the kit may contain an anti-phospho-Erk2 antibody.

Certain embodiments of the invention are directed to methods for screening a test compound (or a lead compound) useful for the treatment or prevention of Alzheimer's disease comprising: contacting cells isolated from a subject diagnosed with Alzheimer's disease with an agent that is a protein kinase C activator, wherein the contacting is done in the presence of the test compound (or a lead compound); measuring the ratio of a phosphorylated first MAP kinase protein to a phosphorylated second MAP kinase protein, wherein the phosphorylated first and phosphorylated second MAP kinase proteins are obtained from the cells after the contacting; measuring the ratio of phosphorylated first MAP kinase protein to phosphorylated second MAP kinase protein in cells from the subject that have not been contacted with the test compound (or a lead compound); subtracting the ratio obtained from the contacting step done in the absence of the test compound (or a lead compound) from the ratio obtained from the contacting step done in the presence of the test compound (or a lead compound); and identifying a test compound (or a lead compound) useful for the treatment of Alzheimer's disease based on the difference in the ratios. In preferred embodiments of the methods for screening a test compound (or a lead compound) useful for the treatment or prevention of Alzheimer's disease, the calculated difference in the ratios is indicative of a test compound (or a lead compound) useful for the treatment of Alzheimer's disease if the difference is a negative value or zero.

In preferred embodiments, the invention is directed to methods for screening a test compound (or a lead compound) useful for the treatment or prevention of Alzheimer's disease wherein the methods comprise an in vitro assay.

In preferred embodiments of the methods for screening a test compound (or a lead compound) useful for the treatment or prevention of Alzheimer's disease the first MAP kinase protein is Erk1 and the second MAP kinase protein is Erk2. In still further preferred embodiments of the invention, the ratios are calculated by dividing the normalized amount of phosphorylated Erk1 by the normalized amount of phosphorylated Erk2. In further embodiments of the invention, the protein kinase C activator is selected from the group consisting of bradykinin, bryostatin, bombesin, cholecystokinin, thrombin, prostaglandin F2α and vasopressin. In further embodiments of the invention, the cells are peripheral cells. In still further embodiments of the invention, the peripheral cells are selected from the group consisting of skin cells, skin fibroblast cells, blood cells and buccal mucosa cells. In still further embodiments of the invention, the cells are not isolated from cerebral spinal fluid. In still further embodiments of the invention, the cells do not comprise cerebral spinal fluid. In still further embodiments of the invention, the cells are not obtained by a spinal tap or lumbar puncture. In still further embodiments of the invention, the protein kinase C activator is contacted with said cells in media comprising serum. In still further embodiments of the invention, the protein kinase C activator is contacted with said cells in serum-free media. In still further embodiments of the invention, the phosphorylated MAP kinase proteins are detected by immunoassay. In still further embodiments of the invention, the immunoassay is a radioimmunoassay, a Western blot assay, an immunofluoresence assay, an enzyme immunoassay, an immunoprecipitation assay, a chemiluminescence assay, an immunohistochemical assay, an immunoelectrophoresis assay, a dot blot assay, or a slot blot assay. In still further embodiments of the invention, the measuring is done using a protein array, a peptide array, or a protein micro array.

In certain embodiments, the invention is directed to methods of monitoring Alzheimer's disease progression in a subject comprising measuring an Alzheimer's disease-specific molecular biomarker. In certain preferred embodiments, the method comprises measuring the Alzheimer's disease-specific molecular biomarker at more than one time point. In preferred embodiements, the Alzheimer's disease-specific molecular biomarker is measured at time points separated by at least six months, more preferably, at time points separated by at least 12 months. In preferred embodiments of the invention, a decrease in the numerical value of the Alzheimer's disease-specific molecular biomarker is indicative of Alzheimer's disease progression in said subject.

In certain embodiments, the invention is directed to compositions useful for the treatment of Alzheimer's disease comprising a compound identified by any of the methods for screening compounds disclosed herein. In preferred embodiments, the compositions of the invention comprise a pharmaceutical composition for treating Alzheimer's disease in a subject in need thereof comprising a therapeutically effective amount of a compound identified by any of the methods for screening compounds disclosed herein.

In certain embodiments, the present invention is directed to methods of treating Alzheimer's disease comprising administering a therapeutically effective amount of any of the pharmaceutical compositions disclosed herein to a subject in need thereof.

DETAILED DESCRIPTION

The present invention relates, in certain aspects, to methods of diagnosing Alzheimer's disease in human cells taken from subjects that have been identified for testing and diagnosis. The diagnosis is based upon the discovery of unique Alzheimer's disease-specific molecular biomarkers. In certain aspects, the invention is directed to methods of monitoring Alzheimer's disease progression and to screening methods for the identification of lead compounds for treating or preventing Alzheimer's disease.

Because direct access to neurons in the brains of living human beings is impossible, early diagnosis of Alzheimer's disease is extremely difficult. By measuring the Alzheimer's disease-specific molecular biomarkers disclosed herein, the present invention provides highly practical, highly specific and highly selective tests for early diagnosis of Alzheimer's disease. In addition, the Alzheimer's disease-specific molecular biomarkers described herein provide a basis for following disease progression and for identifying therapeutic agents for drug development targeted to the treatment and prevention of Alzheimer's disease.

The inventors have found a unique molecular biomarker for Alzheimer's disease using peripheral (non-CNS) tissue that is useful in diagnostic assays that are highly sensitive and highly specific for the diagnosis of Alzheimer's disease. A great advantage of the instant invention is that the tissue used in the assays and methods disclosed herein may be obtained from subjects using minimally invasive procedures, i.e., without the use of a spinal tap. Thus, one aspect of the invention is directed to an assay or test for the early detection of Alzheimer's disease in a subject in which an internally controlled ratio of Erk1 phosphorylation to Erk2 phosphorylation, which is induced by a protein kinase C activator (such as bradykinin), is measured with specific antibodies using a baseline normalization response to growth media in human cells, such as skin fibroblasts, or other peripheral cells such as blood cells.

In the methods of the invention, the cells that are taken from the individual or patient can be any viable cells. Preferably, they are skin fibroblasts, but any other peripheral tissue cell (i.e. outside of the central nervous system) may be used in the tests of this invention if such cells are more convenient to obtain or process. Other suitable cells include, but are not limited to, blood cells such as erythrocytes and lymphocytes, buccal mucosal cells, nerve cells such as olfactory neurons, cerebrospinal fluid, urine and any other peripheral cell type.

In addition, the cells used for purposes of comparison do not necessarily have to be from healthy donors.

The cells may be fresh or may be cultured (see, U.S. Pat. No. 6,107,050, which is herein incorporated by reference in its entirety). In a specific embodiment, a punch skin biopsy can be used to obtain skin fibroblasts from a subject. These fibroblasts are analyzed directly using the techniques described herein or introduced into cell culture conditions. The resulting cultured fibroblasts are then analyzed as described in the examples and throughout the specification. Other steps may be required to prepare other types of cells which might be used for analysis such as buccal mucosal cells, nerve cells such as olfactory cells, blood cells such as erythrocytes and lymphocytes, etc. For example, blood cells can be easily obtained by drawing blood from peripheral veins. Cells can then be separated by standard procedures (e.g. using a cell sorter, centrifugation, etc.) and later analyzed.

Thus, the present invention relates, in certain aspects, to methods for the diagnosis and treatment of Alzheimer's disease in a subject. In certain embodiments, the diagnostic methods of the invention are based on measuring the ratio of two specific and distinct phosphorylated MAP kinase proteins in cells taken from a subject which have been stimulated with an agent that is a protein kinase C activator. The invention is also directed, in certain embodiments, to kits containing reagents useful for the detection or diagnosis of Alzheimer's disease. In certain aspects, the invention is directed to methods for screening to identify lead compounds useful for treating Alzheimer's disease as well as to methods of using these compounds or chemical derivatives of the lead compounds in pharmaceutical formulations to treat or prevent Alzheimer's disease in subjects in need thereof.

I. Definitions

As used herein, the term "sensitivity" in the context of medical screening and diagnosis, means the proportion of affected individuals who give a positive test result for the disease that the test is intended to reveal, i.e., true positive results divided by total true positive and false negative results, usually expressed as a percentage.

As used herein, the term "specificity" in the context of medical screening and diagnosis, means the proportion of individuals with negative test results for the disease that the test is intended to reveal, i.e., true negative results as a proportion of the total of true negative and false-positive results, usually expressed as a percentage.

As used herein, the term "highly sensitive" means a diagnostic method that is greater than or equal to about 50% sensitive, or about 55% sensitive, or about 60% sensitive, or about 65% sensitive, or about 70% sensitive, or about 75% sensitive, or about 80% sensitive, or about 85% sensitive, or about 90% sensitive, or about 95% sensitive, or about 96% sensitive, or about 97% sensitive, or about 98% sensitive, or about 99% sensitive or about 100% sensitive.

As used herein, the term "highly specific" means a diagnostic method that is greater than or equal to about 50% specific, or about 55% specific, or about 60% specific, or about 65% specific, or about 70% specific, or about 75% specific, or about 80% specific, or about 85% specific, or about 90% specific, or about 95% specific, or about 96% specific, or about 97% specific, or about 98% specific, or about 99% specific or about 100% specific.

As used herein, "lead compounds" are compounds identified using the methods of screening compounds disclosed herein. Lead compounds may have activity in shifting the Alzheimer's disease-specific molecular biomarkers disclosed herein to values corresponding to those values calculated for Alzheimer's disease-specific molecular biomarkers determined using normal healthy cells in the assays described herein. Lead compounds may be subsequently chemically modified to optimize or enhance their activity for use in pharmaceutical compositions for the treatment or prevention of Alzheimer's disease.

As used herein, "sequence variants" are proteins that are related to each other both structurally and functionally. In certain embodiments, sequence variants are proteins that share structural similarity at the level of amino acid sequence and share functional attributes at the level of enzymatic activity. In certain embodiments, sequence variants are MAP kinase proteins that catalyze the phosphorylation of other proteins.

II. Methods of Diagnosing Alzheimer's Disease

The present invention is directed, in certain embodiments, to methods of diagnosing Alzheimer's disease. In certain preferred embodiments, the diagnostic methods involve the steps of obtaining a cell sample from a subject, contacting the cell sample with an agent that is a protein kinase C activator and measuring the ratio of specific phosphorylated MAP kinase proteins in said cell sample to diagnose Alzheimer's disease in said subject. In certain specific embodiments, the diagnostic assays disclosed herein may be carried out in vitro or in vivo. In a specific embodiment, the protein kinase C activator is bradykinin. In a further specific embodiment, the ratio of specific phosphorylated MAP kinase proteins is the ratio of phosphorylated Erk1 to phosphorylated Erk2, which is calculated by dividing the relative or normalized amount of phosphorylated Erk1 by the relative or normalized amount of phosphorylated Erk2.

Alzheimer's Disease-Specific Molecular Biomarkers

The diagnostic methods and methods of screening compounds useful for treating Alzheimer's disease which are disclosed herein are based upon the discovery by the inventors of a unique molecular biomarker for Alzheimer's disease. The numerical value of the Alzheimer's disease-specific molecular biomarker will depend on certain variables, such as, for example, the cells used in the assay, the protein kinase C activator used in the assay and the specific MAP kinase proteins that are targeted for measurement of phosphorylation ratios.

In a specific embodiment, the Alzheimer's disease-specific molecular biomarker may be measured by determining the ratio of phosphorylated Erk1 to phosphorylated Erk2 in cells that have been stimulated by a protein kinase C activator and subtracting from this the ratio of phosphorylated Erk1 to phosphorylated Erk2 in cells that have been stimulated with a control solution (vehicle) that lacks the protein kinase C activator. In certain embodiments, if the difference is greater than zero, i.e. a positive value, this is diagnostic of Alzheimer's disease. In further preferred embodiments, if the difference is less than or equal to zero, this is indicative of the absence of Alzheimer's disease.

In other embodiments, the Alzheimer's disease-specific molecular biomarkers of the present invention are measured by determining the ratio of two phosphorylated MAP kinase proteins after stimulation of cells with a protein kinase C activator. The molecular biomarker may be measured by determining the ratio of a first phosphorylated MAP kinase protein to a phosphorylated second MAP kinase protein in cells that have been stimulated by a protein kinase C activator and subtracting from this the ratio of phosphorylated first MAP kinase protein to phosphorylated second MAP kinase protein in cells that have been stimulated with a control solution (vehicle) that lacks the protein kinase C activator. In certain preferred embodiments, if the difference is greater than zero, i.e. a positive value, this is diagnostic of Alzheimer's disease. In further preferred embodiments, if the difference is less than or equal to zero, this is indicative of the absence of Alzheimer's disease.

In certain embodiments, the Alzheimer's disease-specific molecular biomarker is a positive numerical value in cell samples taken from patients diagnosed with Alzheimer's disease (AD cells). In certain preferred embodiments, when the Alzheimer's disease-specific molecular biomarker is measured by determining ratios of phosphorylated Erk1 to phosphorylated Erk2 in AD cells that have been stimulated with bradykinin, the positive numerical values for the Alzheimer's disease-specific molecular biomarker in AD cells may range from about zero to about 0.5.

In certain embodiments, the Alzheimer's disease-specific molecular biomarker is a negative numerical value when measured in cells taken from subjects diagnosed with non-Alzheimer's disease dementia (non-ADD cells), such as, for example, Parkinson's disease or Huntington's disease or Clinical Schizophrenia. In certain preferred embodiments, when the Alzheimer's disease-specific molecular biomarker is measured by determining ratios of phosphorylated Erk1 to phosphorylated Erk2 in non ADD cells that have been stimulated with bradykinin, the negative numerical values may range from about zero to about −0.2 or about −0.3.

In certain embodiments, the Alzheimer's disease-specific molecular biomarker may be a negative numerical value, zero or very low positive numerical value in cell samples from age-matched control cells (AC cells) taken from patients who do not have Alzheimer's disease. When the Alzheimer's disease-specific molecular biomarker is measured by determining ratios of phosphorylated Erk1 to phosphorylated Erk2 in AC cells that have been stimulated with bradykinin, the Alzheimer's disease-specific molecular biomarker in AC cells may range from less than about 0.05 to about −0.2.

In certain embodiments of the invention, the Alzheimer's disease-specific molecular biomarkers may be measured by calculating the ratio of phosphorylated Erk1 to phosphorylated Erk2 in cells that have been stimulated with bradykinin minus the ratio of phosphorylated Erk1 to phosphorylated Erk2 in cells that have stimulated with a solution lacking bradykinin. This is expressed as the following: Alzheimer's disease-specific molecular biomarker=$\{(pErk1/pErk2)_{bradykinin}\}-\{(pErk1/pErk2)_{vehicle}\}$.

Protein Kinase C Activators

Protein kinase C activators that are specifically contemplated for use in the diagnostic methods, kits and methods of screening to identify compounds of the instant invention include, but are not limited to: Bradykinin; α-APP modulator; Bryostatin 1; Bryostatin 2; DHI; 1,2-Dioctanoyl-sn-glycerol; FTT; Gnidimacrin, *Stellera chamaejasme* L.; (−)-Indolactam V; Lipoxin A$_4$; Lyngbyatoxin A, *Micromonospora* sp.; Oleic acid; 1-Oleoyl-2-acetyl-sn-glycerol; 4 α-Phorbol; Phorbol-12, 13-dibutyrate; Phorbol-12, 13-didecanoate; 4α-Phorbol-12, 13-didecanoate; Phorbol-12-myristate-13-acetate; L-α-Phosphatidylinositol-3, 4-bisphosphate, Dipalmitoyl-, Pentaammonium Salt; L-α-Phosphatidylinositol-4, 5-bisphosphate, Dipalmitoyl-, Pentaammonium Salt; L-α-Phosphatidylinositol-3, 4, 5-trisphosphate, Dipalmitoyl-, Heptaammonium Salt; 1-Stearoyl-2-arachidonoyl-sn-glycerol; Thymeleatoxin, *Thymelea hirsuta* L.; insulin, phorbol esters, lysophosphatidylcholine, lipopolysaccharide, anthracycline dannorubicin and vanadyl sulfate. Also included are compounds known as "bryologues." Bryologues are described, for example, in Wender et al. Organic letters (United States) May 12, 2005, 7 (10) p1995-8; Wender et al. Organic letters (United States) Mar. 17, 2005, 7 (6) p1177-80; Wender et al. Journal of Medicinal Chemistry (United States) Dec. 16, 2004, 47 (26) p6638-44. A protein kinase C activator may be used alone or in combination with any other protein kinase C activator in the diagnostic methods, kits and methods of screening compounds disclosed herein.

Bradykinin is a potent vasoactive nonapeptide that is generated in the course of various inflammatory conditions. Bradykinin binds to and activates specific cell membrane bradykinin receptor(s), thereby triggering a cascade of intracellular events leading to the phosphorylation of proteins known as "mitogen activated protein kinase" (MAPK). Phosphorylation of protein, the addition of a phosphate group to a Ser, Thr, or Tyr residue, is mediated by a large number of enzymes known collectively as protein kinases. Phosphorylation normally modifies the function of, and usually activates, a protein. Homeostasis requires that phosphorylation be a transient process, which is reversed by phosphatase enzymes that dephosphorylate the substrate. Any aberration in phosphorylation or dephosphorylation may disrupt biochemical pathways and cellular functions. Such disruptions may be the basis for certain brain diseases.

Measuring or Detecting Levels of Phosphorylated Proteins

The methods of diagnosing Alzheimer's disease and methods of screening compounds to identify agents useful for the treatment or prevention of Alzheimer's disease herein disclosed depend on measuring the Alzheimer's disease-specific molecular biomarkers of the present invention.

In a preferred embodiment, the level of phosphorylated protein present in cells is detected by Western blotting. Protein levels of phosphorylated Erk1 or phosphorylated Erk2 can be measured in fibroblasts using anti-Erk1, anti-Erk2, anti-phospho-Erk1 and anti-phospho-Erk2 antibodies (Cell Signaling Technology). Levels of a different protein may also be measured in the same sample as a reference protein for normalization. Examples of possible reference proteins include, but are not limited to, annexin-II or actin.

In one embodiment, ELISA is performed according to the following procedures: 1) Add fibroblast cell lysates after treatment in duplicates or triplicates to a 96-well microplate that is previously coated with an anti-Erk antibody. 2) Incubate samples in microplate wells at room temperature for about 2 hours. 3) Aspirate samples and wash wells with a phosphate buffered saline (PBS)-based washing buffer. 4) Add working dilution of an anti-phospho-Erk1/2, or an anti-regular Erk1/2 antibody to each well, and incubate at room temperature for about 1 hour. 5) Aspirate and wash well with washing buffer. 6) Add a working dilution of a secondary antibody conjugated with horseradish peroxidase (HRP) to each well and incubate well at room temperature for about 30 min. 7) Aspirate and wash well with washing buffer. 8) Add stabilized Chromogen such as diaminobenzidine (DAB) and incubate at room temperature for about 30 min. 9) Add stop solution and measure the absorbance at 450 nm. Phosphorylation of Erk1/2 is assessed after normalization: $NR=A_P/A_R$. Where NR=the normalized ratio; $A_P$ is absorbance values for phospho-Erk1/2; and $A_R$ is absorbance for the total (regular) Erk1/2.

In a preferred embodiment, phosphorylation of Erk1/2 is assayed on Western blots using an anti-phospho-Erk1/2 antibody. Levels of the immunoreactive signals for phosphorylated Erk1/2 are quantified via densitometric scan. The mean density of the phospho-Erk1/2 signals are normalized with the mean density of total Erk1/2 signals that are detected from the same cell lysate samples with an anti-regular Erk1/2 antibody on a separate Western blot. The formula for normalization is: $NR=D_P/D_R$. Where NR (normalized ratio) represents Erk1/2 phosphorylation extent; $D_P$ is the mean density for phospho-Erk1/2, and $D_R$ is the mean density for the total amount of Erk1/2 detected on a Western blot from the same sample.

Immunoassays of the present invention for the detection of proteins may be immunofluorescent assays, radioimmunoassays, Western blot assays, enzyme immunoassay, immunoprecipitation, chemiluminescent assay, immunohistochemical assay, dot or slot blot assay and the like. (In "Principles and Practice of Immunoassay" (1991) Christopher P. Price and David J. Neoman (eds), Stockton Press, New York, N.Y., Ausubel et al. (eds) (1987) in "Current Protocols in Molecular Biology" John Wiley and Sons, New York, N.Y.). Detection may be by colormetric or radioactive methods or any other conventional methods known to those having skill in the art. Standard techniques known in the art for ELISA are described in *Methods in Immunodiagnosis*, $2^{nd}$ Edition, Rose and Bigazzi, eds., John Wiley and Sons, New York 1980 and Campbell et al., *Methods of Immunology*, W.A. Benjamin, Inc., 1964, both of which are incorporated herein by reference. Such assays may be direct, indirect, competitive, or noncompetitive immunoassays as described in the art (In "Principles and Practice of Immunoassay" (1991) Christopher P. Price and David J. Neoman (eds), Stockton Pres, NY, N.Y.; Oellirich, M. 1984. *J. Clin. Chem. Clin. Biochem.* 22: 895-904 Ausubel, et al. (eds) 1987 in *Current Protocols in Molecular Biology*, John Wiley and Sons, New York, N.Y.

Cell Types, Protein Isolation and Antibodies

As stated previously, the cells taken from the patient being diagnosed may be any cell. Examples of cells that may be used include, but are not limited to, skin cells, skin fibroblasts, buccal mucosal cells, blood cells, such as erythrocytes, lymphocytes and lymphoblastoid cells, and nerve cells and any other cell expressing the Erk1/2 protein. Necropsy samples and pathology samples may also be used. Tissues comprising these cells may also be used, including brain tissue or brain cells. The cells may be fresh, cultured or frozen. Protein samples isolated from the cells or tissues may be used immediately in the diagnostic assay or methods for screening compounds or frozen for later use. In a preferred embodiment fibroblast cells are used. Fibroblast cells may be obtained by a skin punch biopsy.

Proteins may be isolated from the cells by conventional methods known to one of skill in the art. In a preferred method, cells isolated from a patient are washed and pelleted in phosphate buffered saline (PBS). Pellets are then washed with "homogenization buffer" comprising 50 nM NaF, 1 mM EDTA, 1 mM EGTA, 20 µg/ml leupeptin, 50 µg/ml pepstatin, 10 mM TRIS-HCl, pH=7.4, and pelleted by centrifugation. The supernatant is discarded, and "homogenization buffer" is added to the pellet followed by sonication of the pellet. The protein extract may be used fresh or stored at −80° C. for later analysis.

In the methods of the invention, the antibodies used in the disclosed immunoassays may be monoclonal or polyclonal in origin. The phosphorylated and non-phosphorylated Erk1/2 protein or portions thereof used to generate the antibodies may be from natural or recombinant sources or generated by chemical synthesis. Natural Erk1/2 proteins can be isolated from biological samples by conventional methods. Examples of biological samples that may be used to isolate the Erk1/2 protein include, but are not limited to, skin cells, such as, fibroblasts, fibroblast cell lines, such as Alzheimer's disease fibroblast cell lines and control fibroblast cell lines which are commercially available through Coriell Cell Repositories, (Camden, N.J.) and listed in the National Institute of Aging 1991 Catalog of Cell Lines, National Institute of General Medical Sciences 1992/1993 Catalog of Cell Lines [(NIH Publication 92-2011 (1992)].

III. Kits for the Diagnosis of Alzheimer's Disease

It is further contemplated that this invention relates to kits which may be utilized in performing any of the diagnostic tests described above. The kits may contain a single diagnostic test or any combination of the tests described herein. The kits may comprise antibodies which recognize regular Erk1/2 (unphosporylated Erk1 or unphosphorylated Erk2) or phosphorylated Erk1/2 (phosphorylated Erk1 or phosphorylated Erk2). The kits may contain antibodies that recognize regular MAP kinase proteins as well as phosphorylated MAP kinase proteins. The kits may also contain any one or more of the protein kinase C activators disclosed herein (such as, for example, bradykinin or bryostatin). Antibodies may be polyclonal or monoclonal. The kits may contain instruments, buffers and storage containers necessary to perform one or more biopsies, such as punch skin biopsies. The kits may also contain instructions relating to the determination of the ratios used to identify the Alzheimer's disease-specific molecular biomarkers of the instant invention as well as the use of the antibodies or other constituents in the diagnostic tests. The instructions may also describe the procedures for performing a biopsy, such as a punch skin biopsy. The kits may also contain other reagents for carrying out the diagnostic tests such as antibodies for the detection of reference proteins used for normalization. Examples of antibodies that recognize possible reference proteins include, but are not limited to, antibodies that recognize annexin-II or actin. The kits may also include buffers, secondary antibodies, control cells, and the like.

IV. Methods of Screening Compounds Useful in the Treatment or Prevention of Alzheimer's Disease The present invention is also directed to methods to screen and identify substances useful for the treatment or prevention of Alzheimer's disease. According to this embodiment, substances which reverse or improve the Alzheimer's disease-specific molecular biomarkers described herein (i.e. back to levels found in normal cells) would be identified and selected as substances which are potentially useful for the treatment or prevention of Alzheimer's disease.

By way of example, one such method of screening to identify therapeutic substances would involve the steps of contacting sample cells from an Alzheimer's disease patient with a substance being screened in the presence of any of the protein kinase C activators disclosed herein and then measuring any of the Alzheimer's disease-specific molecular biomarkers disclosed herein. An agent that reverses or improves the Alzheimer's disease-specific molecular biomarker back to levels found in normal cells (i.e. cells taken from a subject without Alzheimer's disease) would be identified and selected as a substance potentially useful for the treatment or prevention of Alzheimer's disease.

In certain embodiments, an agent that reverses or improves an Alzheimer's disease-specific molecular biomarker is an agent that causes a reduction of a positive value and/or a movement towards more negative values for an Alzheimer's disease-specific molecular biomarker.

V. Methods of Monitoring the Progression of Alzheimer's Disease

The present invention is also directed to methods of monitoring the progression of Alzheimer's disease in a subject.

Figure 1:
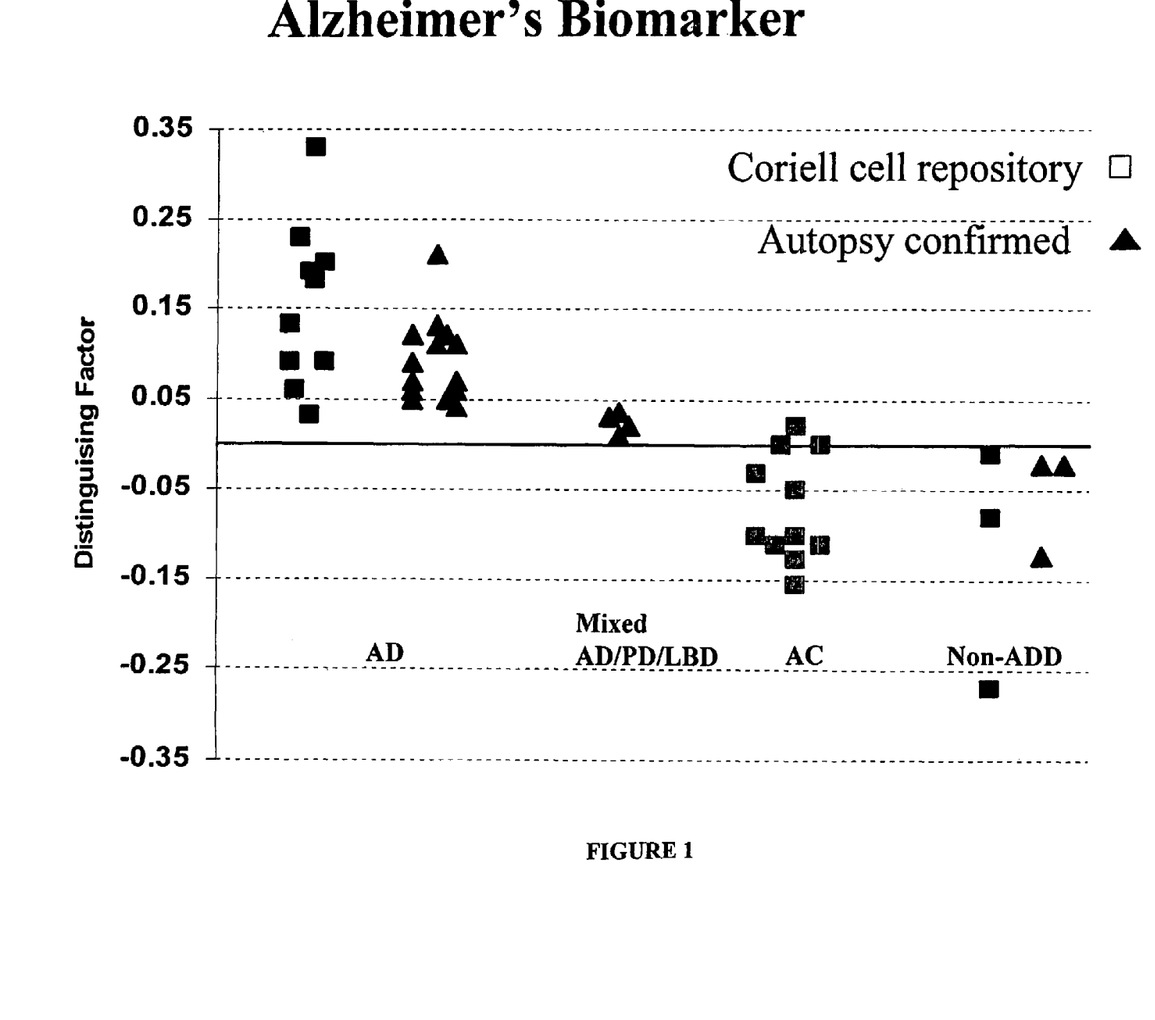
FIG. 1 shows the results of determinations of Alzheimer's disease-specific molecular biomarkers in banked skin fibroblast cells obtained from the Coriell Cell Repository and in punch skin biopsy samples that were immediately placed in tissue culture and which were obtained from Autopsy confirmed subjects. AD refers to Alzheimer's disease cells; Mixed AD/PD/LBD refers to cells taken from patients with mixed pathologies of Alzheimer's disease, Parkinson's Disease and/or Loewi Body disease; AC refers to non-dementia age-matched control cells; Non-ADD refers to cells taken from subjects diagnosed with non-Alzheimer's disease dementia (e.g. Huntington's disease or Parkinsons's disease or Clinical Schizophrenia). The Alzheimer's disease-specific molecular biomarkers in AD cells tested was a positive value falling between greater than about 0.02 and less than about 0.4. The Alzheimer's disease-specific molecular biomarker in Mixed AD/PD/LBD clustered together at very low positive values, i.e. less than about 0.02 or about 0.03. The Alzheimer's disease-specific molecular biomarkers in non-dementia age-matched control cells were negative or very low positive values, i.e. less than about 0.01. The Alzheimer's disease-specific molecular biomarkers in non-ADD cells were negative values. Alzheimer's disease-specific molecular biomarkers were measured by determining the ratio of phosphorylated Erk1 to phosphorylated Erk2 in cells that had been stimulated with bradykinin minus the ratio of phosphorylated Erk1 to phosphorylated Erk2 in cells that were stimulated with media lacking bradykinin. This is expressed as the following: Alzheimer's disease-specific molecular biomarker=$\{(pErk1/pErk2)_{bradykinin}\}-\{(pErk1/pErk2)_{vehicle}\}$.
Figure 2:
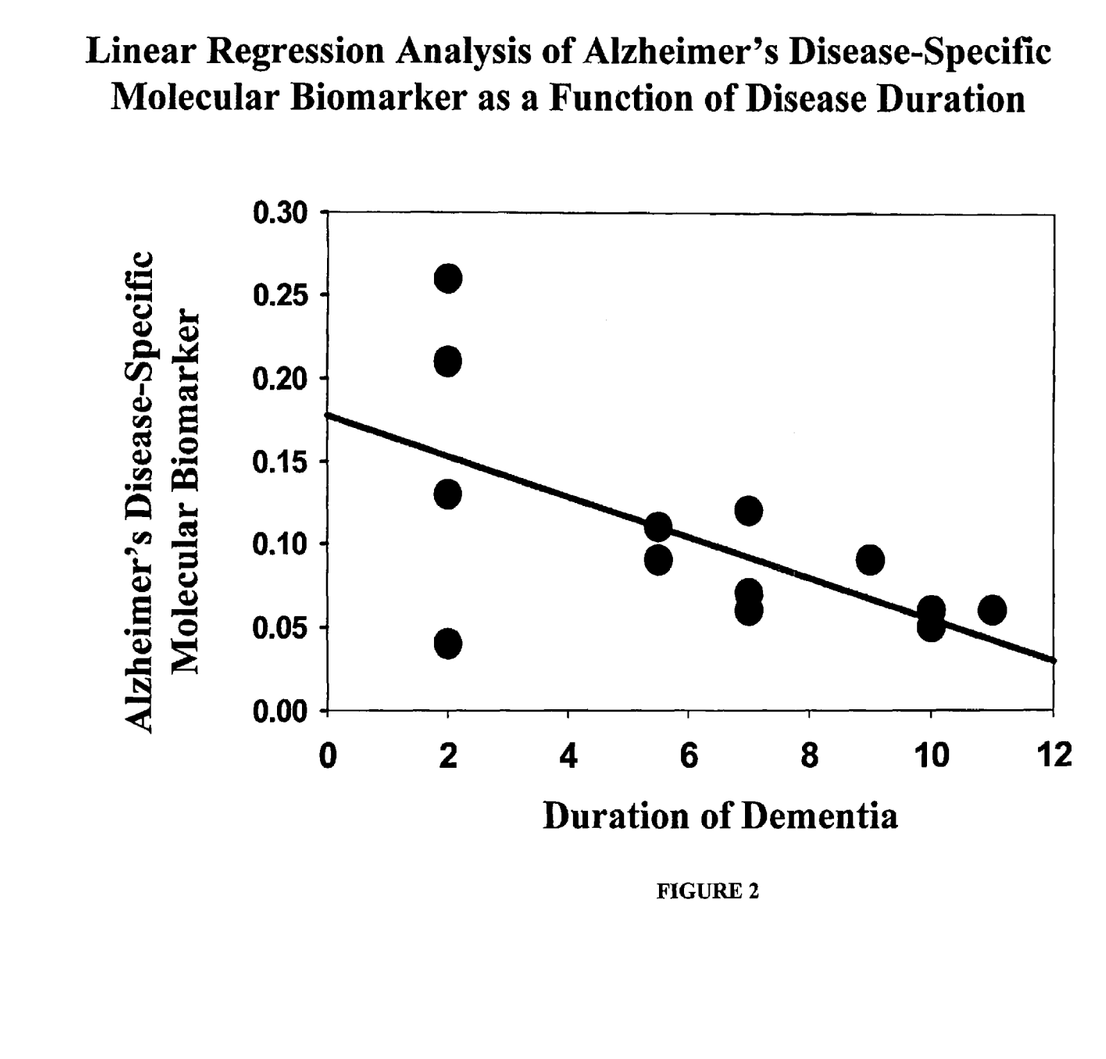
FIG. 2 shows a linear regression analysis of Alzheimer's disease-specific molecular biomarkers as a function of years of dementia. The linear regression shows a negative slope of approximately −0.01 indicating an inverse correlation between years of dementia and positive magnitude of the Alzheimer's disease-specific molecular biomarker. As the years of dementia increases (i.e. as Alzheimer's disease progresses) the Alzheimer's disease-specific molecular biomarker becomes a less positive numerical value. Measurement of the Alzheimer's disease-specific molecular biomarker allows for early diagnosis of Alzheimer's disease because a more highly positive value is indicative of early stages of the disease. Alzheimer's disease-specific molecular biomarkers were measured by determining the ratio of phosphorylated Erk1 to phosphorylated Erk2 in cells that had been stimulated with bradykinin minus the ratio of phosphorylated Erk1 to phosphorylated Erk2 in cells that were stimulated with media lacking bradykinin. This is expressed as the following: Alzheimer's disease-specific molecular biomarker=$\{(pErk1/pErk2)_{bradykinin}\}-\{(pErk1/pErk2)_{vehicle}\}$.

FIG. 2 provides a linear regression analysis of Alzheimer's disease-specific molecular biomarkers as a function of years of duration of dementia. The linear regression shows a negative slope of approximately −0.01 indicating an inverse correlation between years of dementia and positive magnitude of the Alzheimer's disease-specific molecular biomarker. As the years of dementia increases (i.e. as Alzheimer's disease progresses) the Alzheimer's disease-specific molecular biomarker becomes a less positive numerical value. Measurement of the Alzheimer's disease-specific molecular biomarker allows for early diagnosis of Alzheimer's disease because, in certain embodiments, a more highly positive value is indicative of early stages of the disease. In certain embodiments, as Alzheimer's disease progresses in a subject, the Alzheimer's disease specific molecular biomarker becomes a less positive value.

Alzheimer's disease-specific molecular biomarkers, in certain embodiments, are measured by determining the ratio of phosphorylated Erk1 to phosphorylated Erk2 in cells that have been stimulated with bradykinin minus the ratio of phosphorylated Erk1 to phosphorylated Erk2 in cells that have been stimulated with media lacking bradykinin. This is expressed as the following: Alzheimer's disease-specific molecular biomarker=$\{(pErk1/pErk2)_{bradykinin}\}-\{(pErk1/pErk2)_{vehicle}\}$.

VI. Compositions Useful for the Treatment of Alzheimer's Disease

The present invention is also directed to compositions useful for the treatment or prevention of Alzheimer's disease. Compounds identified using the screening methods described herein may be formulated as pharmaceutical compositions for administration to subjects in need thereof.

A pharmaceutical composition of the present invention or a compound (or a chemical derivative of a lead compound) identified using the screening methods disclosed herein can be administered safely by admixing with, for example, a pharmacologically acceptable carrier according to known methods to give a pharmaceutical composition, such as tablets (inclusive of sugar-coated tablets and film-coated tablets), powders, granules, capsules, (inclusive of soft capsules), liquids, injections, suppositories, sustained release agents and the like, for oral, subcutaneous, transdermal, transcutaneous or parenteral (e.g., topical, rectal or intravenous) administration.

Examples of pharmacologically acceptable carriers for use in the pharmaceutical compositions of the invention include, but are not limited to various conventional organic or inorganic carriers, including excipients, lubricants, binders and disintegrators for solid preparations, and solvents, solubilizers, suspending agents, isotonic agents, buffers, soothing agents, and the like for liquid preparations. Where necessary, conventional additives such as antiseptics, antioxidants, coloring agents, sweeteners, absorbents, moistening agents and the like can be used appropriately in suitable amounts.

Examples of excipients for use in the pharmaceutical compositions of the invention include, but are not limited to agents such as lactose, sucrose, D-mannitol, starch, corn starch, crystalline cellulose, light anhydrous silicic acid, polysaccharides, disaccharides, carbohydrates, trehalose and the like.

Examples of lubricants for use in the pharmaceutical compositions of the invention include, but are not limited to agents such as magnesium stearate, calcium stearate, talc, colloidal silica and the like.

Examples of binders for use in the pharmaceutical compositions of the invention include, but are not limited to crystalline cellulose, sucrose, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of disintegrators for use in the pharmaceutical compositions of the invention include, but are not limited to starch, carboxymethylcellulose, carboxymethylcellulose calcium, sodium carboxymethyl starch, L-hydroxypropylcellulose and the like.

Examples of solvents for use in the pharmaceutical compositions of the invention include, but are not limited to water for injection, alcohol, propylene glycol, Macrogol, sesame oil, corn oil, olive oil and the like.

Examples of solubilizers for use in the pharmaceutical compositions of the invention include, but are not limited to polyethylene glycol, propylene glycol, D-mannitol, benzyl benzoate, ethanol, tris-aminomethane, cholesterol, triethanolamine, sodium carbonate, sodium citrate and the like.

Examples of suspending agents for use in the pharmaceutical compositions of the invention include, but are not limited to surfactants such as stearyl triethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like.

Examples of isotonic agents for use in the pharmaceutical compositions of the invention include, but are not limited to glucose, D-sorbitol, sodium chloride, glycerine, D-mannitol and the like.

Examples of buffers for use in the pharmaceutical compositions of the invention include, but are not limited to phosphate, acetate, carbonate, citrate etc., and the like.

Examples of soothing agents for use in the pharmaceutical compositions of the invention include, but are not limited to benzyl alcohol and the like.

Examples of antiseptics for use in the pharmaceutical compositions of the invention include, but are not limited to p-oxybenzoates, chlorobutanol, benzyl alcohol, phenethyl alcohol, dehydroacetic acid, sorbic acid and the like.

Examples of antioxidants for use in the pharmaceutical compositions of the invention include, but are not limited to sulfite, ascorbic acid, $\alpha$-tocopherol and the like.

In certain embodiments when the pharmaceutical composition of the present invention is used as an injection, a carrier for injection to be used may include any or all of the following: a solvent, a solubilizer, a suspending agent, an isotonic agent, a buffer, a soothing agent and the like. Examples of the solvent include, but are not limited to water for injection, physiological saline, Ringer's solution and the like. Examples of the solubilizer include, but are not limited to polyethylene glycol, propylene glycol, D-mannitol, benzyl benzoate, trisaminomethane, cholesterol, triethanolamine, sodium carbonate, sodium citrate and the like. Examples of the isotonic agent include but are not limited to glucose, D-sorbitol, sodium chloride, glycerin, D-mannitol and the like. Examples of the buffer include but are not limited to buffers such as phosphate, acetate, carbonate, citrate and the like, and the like. Examples of the soothing agent include but are not limited to benzyl alcohol and the like. Examples of the pH adjusting agent include but are not limited to hydrochloric acid, phosphoric acid, citric acid, sodium hydroxide, sodium bicarbonate, sodium carbonate and the like.

In certain embodiments, the composition for injection of the present invention may be freeze-dried in an aseptically treated freeze dryer and preserved in a powder state, or can be sealed in a container for injection (e.g., ampoule) and preserved.

In addition, the pharmaceutical composition of the present invention may be diluted with the aforementioned carrier for injection when in use.

The content of an active compound in the pharmaceutical composition of the present invention may vary depending on the form of the preparation, but it is generally about 0.01-about 99 wt %, preferably about 0.1-about 50 wt %, more preferably about 0.5-about 20 wt %, of the whole preparation.

The content of nonionic surfactant in the pharmaceutical composition of the present invention may vary depending on the form of the preparation, but it is generally about 1 to about 99.99 wt %, preferably about 10 to about 90 wt %, more preferably about 10 to about 70 wt %, of the whole preparation.

The content of ethanol, benzyl alcohol or dimethylacetamide in the pharmaceutical compositions of the present invention may vary depending on the form of the preparation, but it is generally about 1 to about 99.99 wt %, preferably about 10 to about 90 wt %, more preferably about 30 to about 90 wt %, of the whole preparation.

The mixing ratio (weight ratio) of nonionic surfactant and ethanol in the pharmaceutical compositions of the present invention is not particularly limited, and is, for example, nonionic surfactant:ethanol=about 0.01-99.99:99.99-0.01, preferably about 1-99:99-1, more preferably about 10-90:90-10 and the like. More preferably, nonionic surfactant:ethanol=about 10-80:90-20, about 50-80:50-20 and the like, and particularly, about 20:80, about 65:35 and the like are preferable.

The content of cyclodextrin derivative readily soluble in water in the pharmaceutical composition of the present invention varies depending on the form of the preparation, but it is generally about 1 to about 99.99 wt %, preferably about 10 to about 99.99 wt %, more preferably about 20 to about 97 wt %, particularly preferably about 50 to about 97 wt %, of the whole preparation.

The content of other additives in the pharmaceutical composition of the present invention may vary depending on the form of the preparation, but it is generally about 1 to about 99.99 wt %, preferably about 10 to about 90 wt %, more preferably about 10 to about 70 wt %, of the whole preparation.

The pharmaceutical compositions of the present invention may be a pharmaceutical composition comprising an active compound, a nonionic surfactant and a cyclodextrin derivative readily soluble in water. In this case, the content of each component, i.e. the active compound, the nonionic surfactant and the cyclodextrin derivative readily soluble in water is the same as in the aforementioned ranges.

VII. Methods of Treating Alzheimer's Disease

The present invention is also directed to methods of treating or preventing Alzheimer's disease using the pharmaceutical compositions disclosed herein.

The compounds of the present invention may be administered by oral, parenteral (for example, intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. The pharmaceutical compositions and method of the present invention may further comprise other therapeutically active compounds which are usually applied in the treatment of Alzheimer's disease.

In the treatment or prevention of Alzheimer's disease an appropriate dosage level will generally be about 0.001 to 100 mg per kg patient body weight per day which can be administered in single or multiple doses. Preferably, the dosage level will be about 0.01 to about 25 mg/kg per day; more preferably about 0.05 to about 10 mg/kg per day. A suitable dosage level may be about 0.01 to 25 mg/kg per day, about 0.05 to 10 mg/kg per day, or about 0.1 to 5 mg/kg per day. Within this range the dosage may be about 0.005 to about 0.05, 0.05 to 0.5 or 0.5 to 5 mg/kg per day. For oral administration, the compositions are preferably provided in the form of tablets containing about 1 to 1000 milligrams of the active ingredient, particularly about 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

All of the references, patents and printed publications mentioned in the instant disclosure are hereby incorporated by reference in their entirety into this application.

The following examples are provided by way of illustration to further describe certain preferred embodiments of the invention, and are not intended to be limiting of the present invention.

EXAMPLES

Example 1

In Vitro Assay of Skin Fibroblasts to Determine Ratio of Phosphorylated Erk1 to Phosphorylated Erk2

Banked skin fibroblasts cells (Alzheimer's disease (AD), non AD dementia (non-ADD) (e.g. Huntington and Parkinson disease and Clinical Schizophrenia) and age-matched control cells (AC), from Coriell Institute of Medical Research were cultured to 90-100% confluence stage. Cells were "starved" in serum-free medium (DMEM) for 16 hours. 10 nM of Bradykinin (BK) in DMSO in regular medium was added at 37° C. for 0 and 10 min. For the controls, the same amount of DMSO was added.

After washing four times with cold (4° C.) 1×PBS, flasks were kept in dry ice/ethanol mixture for 15 min. Flasks were removed from dry ice/ethanol mixture and then 80 µL of lysis buffer (10 mM Tris, pH 7.4, 150 mM NaCl, 1 mM EDTA, 1 mM EGTA, 0.5% NP-40, 1% Triton X-100, 1% protease inhibitor cocktail, 1% ser/thr/tyrosine phosphatase inhibitor cocktails) was added into each flask.

Flasks were kept on an end-to-end shaker in a cold room (4° C.) for 30 min and cells were collected from each flask with a cell scraper. Cells were sonicated and then centrifuged at 14000 rpm for 15 min, and the supernatant was used for Western blotting after total protein assay.

Total Erk1, Erk2 and the phosphorylated forms of Erk1 and Erk2 (p-Erk1, p-Erk2) were determined using specific antibodies: anti-regular Erk1/2 and anti-phospho ERK1/2.

Example 2

Skin Fibroblasts

Banked skin fibroblasts from patients with AD and age-matched controls are purchased from the Coriell Institute for Medical Research. Autopsy confirmed skin fibroblasts are obtained separately. Patients may be clinically affected with severe dementia, progressive memory loss, and other impaired cognitive functions. Brains from these patients show abnormal EEG and different degrees of cerebral atrophy by CAT or CT scan. Cells from normal individuals with close age matches are used as controls.

Fresh-taken skin fibroblasts. The collection and culture of fibroblasts from freshly obtained skin tissue is performed as follows: Punch-biopsy skin tissues from non-FAD (NFAD) patients and age-matched controls are obtained by qualified personnel. All patients (or representatives) sign informed consent forms.

Banked fibroblasts from Huntington's disease. These fibroblasts are from Huntington's disease (HD) patients, with dementia accompanying typical Huntington's disease symptoms. Fibroblasts from normal age-and gender-matched individuals are used as controls.

Example 3

Materials

DMEM is purchased from Gibco BRL. Fetal bovine serum is purchased from Bio Fluids. Bradykinin, diphenylboric acid 2-aminoethyl ester (2ABP), protease, and phosphatase inhibitor cocktails are purchased from Sigma; bisindolylmaleimide-1 and LY294002 are purchased from Alexis; PD98059 is purchased from Cell Signaling Technology. Anti-phospho-Erk1/2 antibodies are purchased from Cell Signaling Technology. Anti-regular Erk1/2 is purchased from Upstate Biotechnology. SDS minigels (4-20%) are purchased from Invertrogene-Novex. Nitrocellulose membranes are purchased form Schleicher & Schuell (Keene, N.H.). All the SDS electrophoresis reagents are purchased from Bio-Rad. The SuperSignal chemilumines-cence substrate kit is purchased from Pierce.

Example 4

Culture of AC and AD Fibroblast Cells

Banked fibroblasts from Alzheimer's disease patients including both FAD and NFAD types, and from age-matched controls (AC), are maintained and cultured in T25/T75 flasks with DMEM containing 10% fetal bovine serum (FBS). Cells are used within passages 6 to 17.

Example 5

Processing and Culture of Fibroblasts from Fresh Biopsy Tissue

Samples are placed in 1×PBS and transported in transfer medium to the laboratory for propagation. After the transfer medium is removed, the skin tissues are rinsed with PBS and finely chopped into 1-mm-sized explants. The explants are transferred one by one onto the growth surface of vented T25 flasks with 3 ml of biopsy medium containing 45% FBS and 100 U/ml penicillin and 100 U/ml streptomycin (Pen/Strep). The tissues are cultured at 37 C for 24 h before addition of 2 ml of biopsy medium containing 10% FBS. The medium is replaced after 48 h with 5 ml of regular culture medium containing 10% FBS and 100 U/ml Pen/Strep. The cells are then passaged and maintained according to a regular procedure given above.

Example 6

Treatment of Fibroblast Cells with Different Protein Kinase C Activators

Bradykinin or different specific protein kinase C activators are used to treat fibroblasts. Banked AC and AD skin fibroblasts are cultured to 80-100% confluence before they are "starved" in serum-free DMEM overnight. Cells are treated with 10 nM protein kinase C activator at 37 C for different lengths of time to establish a time course for the protein kinase C acivator-induced effects. The time point at which reactions are terminated immediately after application of protein kinase C activator is defined as "0 min" post-protein kinase C activator treatment. A control flask of cells for each cell line at each treatment time point is added with the identical volume of PBS. The reaction is terminated by removing the culture medium, rapidly rinsing the cells with precooled PBS, pH 7.4, and transferring the flask onto dry ice/ethanol. For cells obtained and cultured from fresh biopsy tissues, a concentration of 0.1 nM protein kinase C activator may be used. The treatment time is about 10 min at 37 C.

To prepare cell lysates from the treated cells, flasks are moved from dry ice/ethanol onto water ice. To each flask is added 1 ml of lysis buffer containing 10 mM Tris, pH 7.4, 150 mM NaCl, 1 mM EDTA, 1 mM EGTA, pH 8, 0.5% NP-40, 1% Triton X-100, 1% protease inhibitor cocktail (Sigma), 1% Ser/Thr, and tyrosine phosphatase inhibitor cocktails (Sigma). After rocking on an end-to-end shaker in a cold room for 30 min, cells are collected from each flask with a cell scraper. Cells are sonicated and centrifuged at 5000 rpm for 5 min, and the supernatant used for Western blotting.

Example 7

Western Blotting

Cell lysates are treated with an equal volume of 2×SDS-sample buffer and boiled for 10 min. Proteins from each sample are resolved on a 4-20% mini-gradient gel and transferred onto a nitrocellulose membrane. Phosphorylated Erk1/2 is detected with an anti-phospho-Erk1/2 antibody using the SuperSignal ECL detection kit. In order to normalize the amount of phosphyorylated Erk1/2 against the total amount of Erk1/2, after being blotted with an anti-phospho-Erk1/2 antibody, the same membrane is stripped with a stripping buffer containing 62.5 mM Tris-HCl, pH 6.7, 2% SDS, and 100 mM 2-mercaptoethanol at 60 C for 45 min and then blotted with an anti-regular Erk1/2 antibody. Alternatively, duplicate samples resolved on SDS-PAGE and transferred to a nitrocellulose membrane are respectively blotted with anti-phospho- and anti-regular Erk antibodies. After being washed with 10 mM PBS, pH 7.4, containing 0.01% Tween 20 (three times for 10 min), the membrane is blotted with an anti-regular Erk1/2 antibody, from which the total amount of Erk1/2 loaded on the SDS gel is measured.

Example 8

Data Analysis

Signals for both phosphorylated and regular forms of Erk1/2 are scanned with a Fujifilm LAS-1000 Plus scanner. The mean optical density of each protein band is measured using NIH Image software. Values from the phospho-Erk1/2 signals are normalized respectively against those of the total Erk1/2 signals. After normalization, data from each treated cell line is converted to a percentage of the basal control and subjected to statistical analyses.

Example 9

Immunocytochemistry

Fibroblast cells are grown on the surface of 2.5-cm-diameter glass coverslips coated with 0.02 mg polylysine. Upon treatment with bradykinin or another protein kinase C activator as described above, cells are rapidly rinsed with cold PBS, pH 7.4, and fixed with 4% formaldehyde in PBS, pH 7.4, at room temperature for 15 min. After being washed with PBS, pH 7.4, three times, each lasting 5 min, cells are penetrated with 0.1% Triton x-100 in PBS, pH 7.4, at room temperature for 30 min. After incubation with 10% normal horse serum in PBS, pH 7.4, at room temperature for 30 min, cells are incubated with anti-phospho-Erk1/2 antibody (1:200) at 4° C. overnight. Cells on the coverslips are washed with PBS, pH 7.4, three times and then an anti-mouse IgG labeled with fluorescein (Vector Laboratories) is added (1:200) and incubated with the cells at room temperature for 60 min. Following three washes with PBS, and sealing with Vectashield (Vector Laboratories), immunostaining signals in the cells are observed with a Nikon fluorescene microscope. The intensity of the immunocytochemistry signals in the cell images is measured with Bio-Rad Quantity One software (BioRad) and Tnimage. For localization of the BK or protein kinase C activator receptors in the skin fibroblasts, a monoclonal anti-BK B2 antibody, or anti protein kinase C activator antibody is applied to the normal fibroblasts, followed by incubation with Cy5-conjugated anti-mouse IgG. The resulting immunoreactive signals are imaged with a fluorescence microscope.

The invention claimed is:

1. A method of diagnosing Alzheimer's disease in a subject comprising the steps of contacting cells obtained from said subject with an agent that is a protein kinase C activator and measuring the ratio of specific phosphorylated MAP kinase proteins in said cells to diagnose Alzheimer's disease in said subject, wherein said ratio of specific phosphorylated MAP kinase proteins is the ratio of phosphorylated Erk1 to phosphorylated Erk2 and is calculated by dividing the normalized amount of phosphorylated Erk1 by the normalized amount of phosphorylated Erk2.

2. The method of claim 1, wherein said protein kinase C activator is selected from the group consisting of bradykinin, bryostatin, bombesin, cholecystokinin, thrombin, prostaglandin F2α and vasopressin.

3. The method of claim 1, wherein said cells are peripheral cells.

4. The method of claim 3, wherein said peripheral cells are selected from the group consisting of skin cells, skin fibroblast cells, blood cells and buccal mucosa cells.

5. The method of claim 1, wherein said cells are not isolated from cerebral spinal fluid.

6. The method of claim 1, wherein said cells do not comprise cerebral spinal fluid.

7. the method of claim 1, wherein said cells are not obtained by a spinal tap or lumbar puncture.

8. The method of claim 1, wherein said protein kinase C activator is contacted with said cells in media comprising serum.

9. The method of claim 1, wherein said protein kinase C activator is contacted with said cells in serum-free media.

10. The method of claim 1 wherein said phosphorylated MAP kinase proteins are detected by immunoassay.

11. The method of claim 10, wherein said immunoassay is a radioimmunoassay, a Western blot assay, an immunofluoresence assay, an enzyme immunoassay, an immunoprecipitation assay, a chemiluminescence assay, an immunohistochemical assay, an immunoelectrophoresis assay, a dot blot assay, or a slot blot assay.

12. The method of claim 1, wherein said measuring is done using a protein array, a peptide array, or a protein micro array.

13. A method of diagnosing Alzheimer's disease in a subject comprising the steps of:
    a) contacting cells from said subject with an agent that is a protein kinase C activator;
    b) measuring the ratio of a phosphorylated first MAP kinase protein to a phosphorylated second MAP kinase protein, wherein said phosphorylated first and second MAP kinase proteins are obtained from said cells after said contacting step;
    c) measuring the ratio of phosphorylated first MAP kinase protein to phosphorylated second MAP kinase protein in cells from said subject that have not been contacted with the agent that is a protein kinase C activator used in step(a);
    d) subtracting the ratio obtained in step (c) from the ratio obtained in step (b);
    e) diagnosing the presence of Alzheimer's disease in said subject based on the difference calculated in step (d),
    wherein said MAP kinase protein is Erk1 and said second MAP kinase protein is Erk2.

14. The method of claim 13, wherein the difference obtained in step (d) is diagnostic of Alzheimer's disease in said subject if the difference is a positive value.

15. The method of claim 13, wherein the difference obtained in step (d) indicates the absence of Alzheimer's disease in said subject if the difference is a negative value or zero.

16. The method of claim 13, wherein said ratios are calculated by dividing the normalized amount of phosphorylated Erk1 by the normalized amount of phosphorylated Erk2.

17. The method of claim 13, wherein said protein kinase C activator is selected from the group consisting of bradykinin, bryostatin, bombesin, cholecystokinin, thrombin, prostaglandin F2α and vasopressin.

18. The method of claim 13, wherein said cells are peripheral cells.

19. The method of claim 18, wherein said peripheral cells are selected from the group consisting of skin cells, skin fibroblast cells, blood cells and buccal mucosa cells.

20. The method of claim 13, wherein said cells are not isolated from cerebral spinal fluid.

21. The method of claim 13, wherein said cells do not comprise cerebral spinal fluid.

22. The method of claim 13, wherein said cells are not obtained by a spinal tap or lumbar puncture.

23. The method of claim 13, wherein said protein kinase C activator is contacted with said cells in media comprising serum.

24. The method of claim 13, wherein said protein kinase C activator is contacted with said cells in serum-free media.

25. The method of claim 13 wherein said phosphorylated MAP kinase proteins are detected by immunoassay.

26. The method of claim 25, wherein said immunoassay is a radioimmunoassay, a Western blot assay, an immunofluoresence assay, an enzyme immunoassay, an immunoprecipitation assay, a chemiluminescence assay, an immunohistochemical assay, an immunoelectrophoresis assay, a dot blot assay, or a slot blot assay.

27. The method of claim 13, wherein said measuring is done using a protein array, a peptide array, or a protein micro array.

28. A method for screening a test compound to determine if the compound is useful for the treatment of Alzheimer's disease comprising:
   a) contacting cells isolated from a subject diagnosed with Alzheimer's disease with an agent that is a protein kinase C activator, wherein said contacting is in the presence of the test compound;
   b) measuring the ratio of a phosphorylated first MAP kinase protein to a phosphorylated second MAP kinase protein, wherein said phosphorylated first and second MAP kinase proteins are obtained from said cells after said contacting in step (a);
   c) measuring the ratio of phosphorylated first MAP kinase protein to phosphorylated second MAP kinase protein in cells from said subject that have not been contacted with the test compound of step (a);
   d) subtracting the ratio obtained in step (c) from the ratio obtained in step (b);
   e) identifying a test compound useful for the treatment of Alzheimer's disease based on the difference calculated in step (d), wherein said first MAP kinase protein is Erk1 and said second MAP kinase protein is Erk2.

29. The method of claim 28, wherein the difference calculated in step (d) is indicative of a test compound useful for the treatment of Alzheimer's disease if said difference is a negative value or zero.

30. The method of claim 28, wherein said ratios are calculated by dividing the normalized amount of phosphorylated Erk1 by the normalized amount of phosphorylated Erk2.

31. The method of claim 28, wherein said protein kinase C activator is selected from the group consisting of bradykinin, bryostatin, bombesin, cholecystokinin, thrombin, prostaglandin F2α and vasopressin.

32. The method of claim 28, wherein said cells are peripheral cells.

33. The method of claim 28, wherein said peripheral cells are selected from the group consisting of skin cells, skin fibroblast cells, blood cells and buccal mucosa cells.

34. The method of claim 28, wherein said cells are not isolated from cerebral spinal fluid.

35. The method of claim 28, wherein said cells do not comprise cerebral spinal fluid.

36. The method of claim 28, wherein said cells are not obtained by a spinal tap or lumbar puncture.

37. The method of claim 28, wherein said protein kinase C activator is contacted with said cells in media comprising serum.

38. The method of claim 28, wherein said protein kinase C activator is contacted with said cells in serum-free media.

39. The method of claim 28 wherein said phosphorylated MAP kinase proteins are detected by immunoassay.

40. The method of claim 39, wherein said immunoassay is a radioimmunoassay, a Western blot assay, an immunofluoresence assay, an enzyme immunoassay, an immunoprecipitation assay, a chemiluminescence assay, an immunohistochemical assay, an immunoelectrophoresis assay, a dot blot assay, or a slot blot assay.

41. The method of claim 28, wherein said measuring is done using a protein array, a peptide array, or a protein micro array.

* * * * *